(12) United States Patent
Ennen et al.

(10) Patent No.: US 6,317,627 B1
(45) Date of Patent: Nov. 13, 2001

(54) ANESTHESIA MONITORING SYSTEM BASED ON ELECTROENCEPHALOGRAPHIC SIGNALS

(75) Inventors: David W. Ennen; Jorge R. Jimenez, both of N. Billerica; Dominic P. Marro, North Andover, all of MA (US)

(73) Assignee: Physiometrix, Inc., N. Billerica, MA (US)

( * ) Notice: Subject to any disclaimer, the term of this patent is extended or adjusted under 35 U.S.C. 154(b) by 0 days.

(21) Appl. No.: 09/431,632

(22) Filed: Nov. 2, 1999

(51) Int. Cl.[7] .................................................. A61B 5/04
(52) U.S. Cl. ......................... 600/544; 600/300; 600/545
(58) Field of Search .................................. 600/544–545, 600/26, 300

(56) References Cited

U.S. PATENT DOCUMENTS 5,813,993 * 9/1998 Kaplan et al. ........................ 600/26
6,067,467 * 5/2000 John ..................................... 600/544
6,230,049 * 5/2001 Fischell et al. ....................... 600/544

* cited by examiner

Primary Examiner—John P. Lacyk
Assistant Examiner—Ryan Carter
(74) Attorney, Agent, or Firm—Frederick C. Williams; Williams & Associates

(57) ABSTRACT

A system which classifies patients according to their level of awareness or consciousness using measures derived solely from electroencephalograph (EEG) signals. The system comprises multiple observers of characteristics of signals, including artifact detectors, especially magnitude artifact detectors, eye blink detectors, stationarity/RMS detectors, slew rate detectors, and burst suppression detectors, and determination of power in certain frequency bands. The system produces a single derived probabilistic measure of conscious awareness called the patient state index (PSI) and displays values of trends in that index and values of an artifact index, an EMG index, and a suppression ratio in order to give the operator current information on the quality of the signal input. The PSI is derived from a statistical analysis using empirically derived population norms and other parameters.

18 Claims, 9 Drawing Sheets

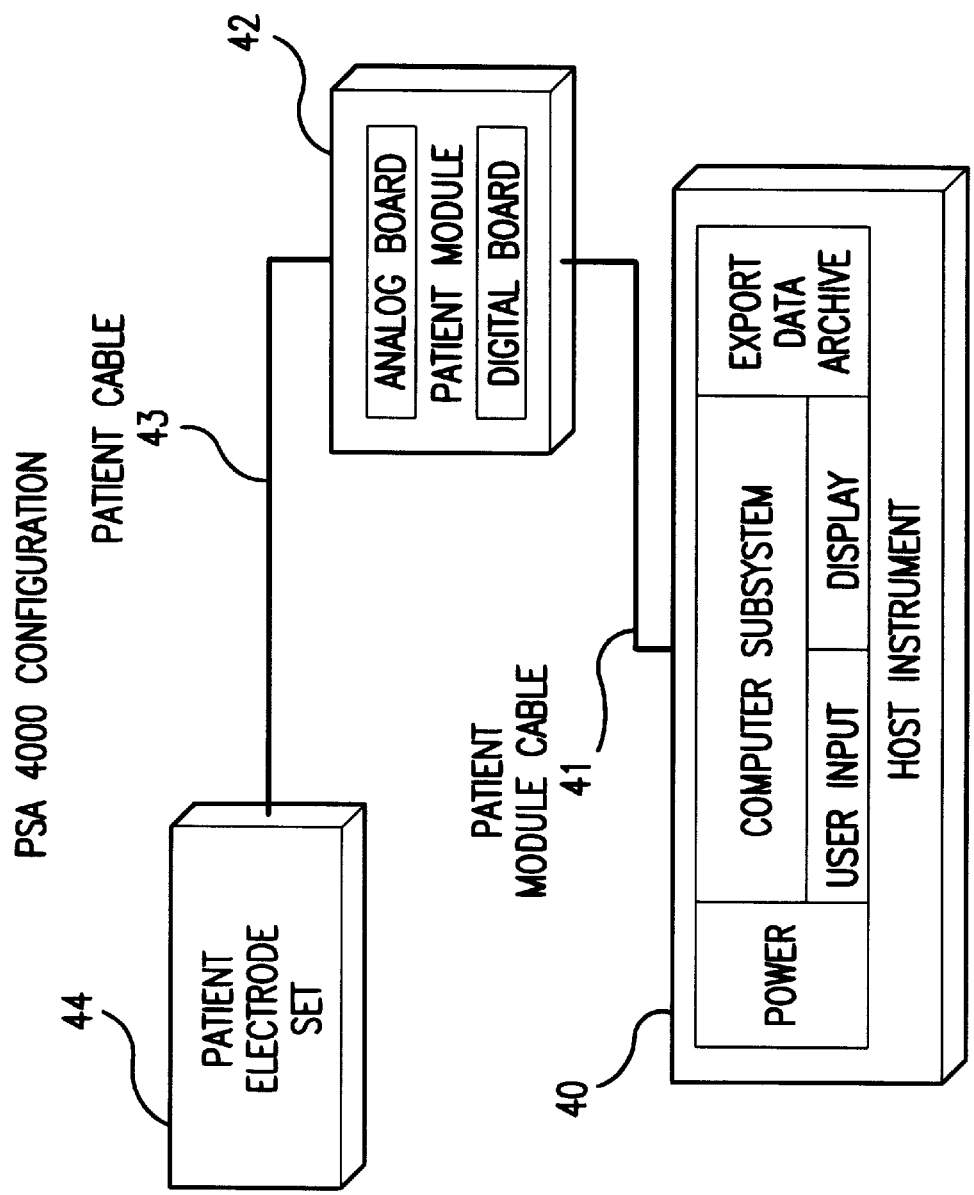

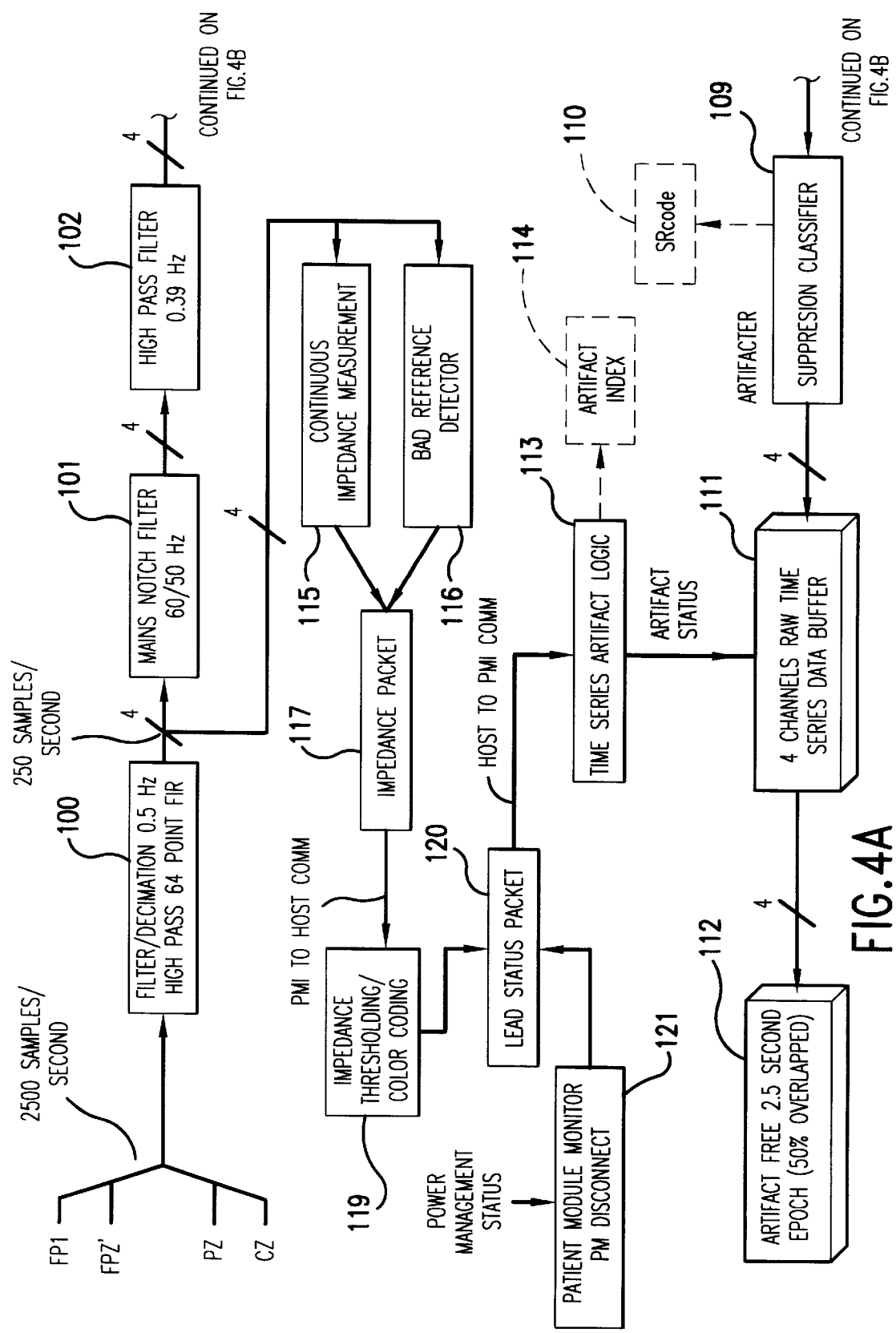

ANESTHESIA MONITORING SYSTEM BASED ON ELECTROENCEPHALOGRAPHIC SIGNALS

FIELD OF THE INVENTION

The current invention relates to the field of medical anesthesia. More particularly it relates to the field of electronic monitoring of patients undergoing anesthesia, especially for use during and after surgical operations. The invention relates more specifically to the use of electroencephalograph (EEG) signals for electronically monitoring a patient's state of awareness.

BACKGROUND OF THE INVENTION

In current medical practice, at least for highly invasive surgery, a patient is placed under general anesthesia. Anesthesiology is a medical art practiced in the United States by and large by board certified physicians (anesthesiologists) and nurses (nurse anesthetists) specifically trained to administer anesthetic drugs and monitor patients under anesthesia. The state of patient anesthesia is attained by the controlled administration of various drugs with known anesthetic properties. These drugs cause the patient to lose consciousness, sensation, and motor control. The physician monitors the patient's state of awareness by means of a number of disparate clinical signs known empirically to provide useful and reliable information about the patient's state of unconsciousness.

Generally, the patient is anesthetized prior to surgery by the specialized medical practitioner (anesthesiologist or nurse anesthetist), who administers one or more vapors or gases by inhalation or introduces anesthetic drugs intravenously. Volatile substances include nitrous oxide, sevoflurane, desflurane, isoflurane, and halothane. Intravenous anesthetics include pentothal, propofol, methohexital, and etomidate.

A correctly administered general anesthetic should remove any sensation of pain and any awareness of the operation itself. (Patients insufficiently deeply anesthetized have reported terror at becoming aware of the surgical procedure while paralyzed.)

The anesthetic should further disable the patient's motor control so that the patient cannot move. Otherwise, the patient may exhibit involuntary (reflex) muscle movements, which can disturb the area being surgically manipulated. Prevention of movement can be accomplished by anesthetic agents acting on the central nervous system or with a blockade of the neuromuscular junction with muscle relaxants.

Finally, the anesthesia must avoid depressing the patient's blood pressure so much as to reduce blood flow to the brain to a dangerous extent. Generally 50 mm Hg for mean arterial pressure is a lower limit.

A trained anesthesiologist or nurse anesthetist will monitor the patient's vital signs such as respiration and pulse rates, check the patient's pupil dilation, and check certain reflexes, such as the lash reflex, and other physiological signs to estimate the depth of anesthesia. In some instances, however, either the practitioner does not have access to all of the required clinical information or other circumstances intervene. For example, in some procedures the patient is draped in such a way as to make observation of some clinical indicators difficult or impossible. In addition, in very lengthy procedures the attention of even the best practitioner can flag.

In such circumstances it would frequently be useful to have an electronic monitor to track the patient's level of consciousness. In particular, it sometimes would be useful to have an instrument, which, once the plane of anesthesia is established qualitatively by the anesthesiologist using traditional clinical indicators, would indicate significant changes in the patient's state of anesthesia or patient responses to stimuli, which would indicate insufficient anesthesia.

A number of inventors have developed systems for using EEG signals, generally in combination with other signals, to monitor anesthesia, sleep, or other states on the consciousness-unconsciousness continuum. Kaplan et al., U.S. Pat. No. 5,813,993, issued Sep. 29, 1998, disclosed a drowsiness detection system based on EEG signals. This invention relies heavily on frequencies in EEG signals above 30 Hz. It does not use any form of norming and in addition applies an ad hoc weighted sum of inverted spectral power coefficients. Maynard, U.S. Pat. No. 5,816,247, issued Oct. 6, 1998, uses a combination of time domain amplitude envelope analysis and frequency analysis in conjunction with a trainable neural network to classify awareness and sleep states. Kangas et al., U.S. Pat. No. 5,775,330, issued Jul. 7, 1998, uses transform processing and neural net analysis to classify states of anesthesia. The output of the neural net could be used to produce a single index of awareness. However, all of these prior art systems either represent an unnecessary level of complexity or an absence of empirical basis or both.

A prior patent to John, U.S. Pat. No. 5,699,808, issued Dec. 23, 1997, discloses a system to monitor multiple patients simultaneously in the surgical recovery room or in intensive care. This system, however, combines certain features of EEG signals and other features including those of evoked potentials to arrive at an estimate of the patient's state of consciousness. It specifically incorporates the use of electrocardiograph (EKG) and electromyograph (EMG) electrodes and also input from a blood pressure detector and from a respiration monitor. This prior art system also requires evoked potentials, specifically Brainstem Auditory Evoked Response (BAER) and Brainstem Somatosensory Evoked Response (BSER). Use of evoked potentials, however, involves the use of additional disposables and a longer set-up time. Further, this system relies very heavily on self-norming and in particular on updating self-norming depending on the state of the patient.

An earlier patent to the same inventor, John, U.S. Pat. No. 4,557,270, issued Dec. 10, 1985, suffered from additional and more severe limitations since it required measurement of blood temperatures and volumes. Finally, John, U.S. Pat. No. 4,545,388, issued Oct. 8, 1985, disclosed the basic process of self-norming of processed EEG data.

Another inventor, Prichep, U.S. Pat. No. 5,083,571, issued Jan. 28, 1992, disclosed a significant advance in the utilization of EEG signals for diagnostic purposes. Prichep disclosed the use of discriminant analysis to sharpen the diagnostic capability of quantities derived from EEG signals with respect to certain well-known diagnostic categories of psychiatric illness. This work compared quantities derived from a patient with parameters derived from populations of persons thought to suffer from specific identified illnesses.

Finally, another patent issued to John, U.S. Pat. No. 6,067,467, issued May 23, 2000, applied discriminant analysis to the statistical differentiation of unconscious from conscious states from EEG signals. However, this invention relied heavily on BAER and BSER signals and self-norming. In addition, this invention stated, with respect to Chamoun, U.S. Pat. No. 5,010,891, issued Apr. 30, 1991, that "the comparison of patients with a normal group, in itself, is not believed to provide reliable information in the surgical context of determining if a patient will be sufficiently anesthetized." App. at p. 4. Since that time, however, the current inventors have learned from further investigation and experimentation that population-norming is sufficiently reliable and self-norming adds unnecessarily to the complexity of the system without adding to performance. What is therefore most lacking in all of these prior art inventions is simplicity and cost effectiveness.

It is therefore an object of the current invention to provide an EEG based anesthesia monitoring system that completely avoids use of transducers for and inputs from other than EEG signals, that is, avoids the use of pulse, blood pressure, and respiration rate sensors and leads. It is a further object of this invention to provide an anesthesia monitoring system based on EEG signals, which completely avoids the need for BAER and BSER stimulation and response monitoring. It is a further object of this invention to provide an EEG based anesthesia monitoring system which dispenses with the cumbersome and error prone process of self-norming. It is another object of this invention to provide an EEG based anesthesia monitoring system which utilizes sample population-norming.

SUMMARY OF THE INVENTION

The current invention comprises a system for using EEG signals to monitor the state of anesthesia of a patient at various stages preparatory to, during, and after administration of anesthetic and surgical operation, and in intensive care during recovery from the operation and anesthesia. The system comprises a headset attached to a patient, a patient module connected to the headset, apparatus for transmitting EEG signals to an analysis unit, and the analysis unit itself. The analysis unit further comprises a number of subsystems, but its essence is the Algorithm which processes the EEG signals into a parameter usable to estimate and/or track the patient's state of unconsciousness or consciousness while under anesthesia.

The primary function of the analysis unit is to classify anesthetized patients according to their conscious state, as determined from an analysis of volunteer data using the OAA/S scale. The version of this scale used in this invention is:

| Modified Observer's Assessment of Alertness/Sedation Scale | |
|---|---|
| Response | Score |
| Responds readily to name spoken in a normal tone | 5 |
| Lethargic response to name spoken in a normal tone | 4 |
| Responds only after name is called loudly and/or repeatedly | 3 |
| Responds only after mild shaking or prodding | 2 |
| Responds only to noxious stimulus and not to mild shaking or prodding | 1 |
| Does not respond to noxious stimulus | 0 |
| Burst Suppression | -1 |

The design of the analysis unit is based on the Multiple Observer Derived Measurement Model depicted in FIG. 1. An observer is a thread of execution and logic, an algorithm, which processes a stream of data and generates a measure of a characteristic(s) identified within the data stream. The principle is that is easier to construct individual observers tuned to specific characteristics in the data stream, than to create one observer that is tuned to classify an ensemble of characteristics in the data stream. Observers 3 are classifier functions that detect signatures within the information. These signatures may be in the time domain, frequency domain, or a combination of the two domains. By tuning observers to specific signatures, selective filtering can be employed to improve the accuracy and latency of an observer. What may be noise to one observer may be critical information to another. This selective filtering increases the overall utilization of the acquired physiological information and thereby improving the performance of the final derived measure.

An Observer Mediator 4 is responsible for logically combining these individual observations in to the single Derived Parameter. The Observer Mediator can weigh the individual observations by monitoring each observer's input signal quality and the context of the observation based on the patient state. The patient state is derived from the behavior of the derived parameter over time and this is fed back to the Observer Mediator. Functionally, either on demand or on a periodic basis, the Observer Mediator polls the Observers and based on patient state and the 'quality' of the individual observations, combines the observations into a single derived measure. The Derived Parameter may be enhanced in sensitivity or scope by either further tuning of established Observers or adding additional Observers.

The primary output of the PSA 4000 algorithm is a single derived parameter called the Patient State Index (PSI) that maps to the OAA/S scale independent of anesthetic agent. The implementation of the Multiple Observer Model for this measure of state of consciousness, the PSI, is shown in FIG. 2. In this system, electroencephalograph (EEG) signals are acquired from an array of electrodes on the patient's scalp. These raw EEG signals are filtered and decimated to reduce external noise and to satisfy data sampling rate (Nyquist) requirements.

Following decimation, artifact analysis takes place. The EEG data is analyzed for validity and contamination. This step results in the setting of various artifact codes. After artifact analysis, the Eye-blink Observer and the Suppression Observer operate. This is followed by the calculation of the Artifact Index and the Suppression Ratio Index. For the FFT calculations, The Fast Fourier Transform (FFT) of the EEG data is calculated for each of the four channels. At this point, the system decomposes the Frequency Spectrum. In this operation the FFT spectral data is divided into frequency bands. After this, the EMG Index is calculated, and the EMG Beta-5 observer operates. The Discriminant Observer then makes its calculations, resulting in a Probability of Correct Classification based on parameters derived from sample populations. Finally, the Observer mediator combines the probability with other the output of the other three observers to the Patient State Index (PSI).

The processing analyzes information in the 0.5 Hz to 50 Hz frequency range. As shown in FIG. 2, the sample data streams are divided into two primary streams: the FP1 channel is separately processed by the Beta5 Observer, all channels [FP1, FPz', Pz, Cz] are processed by an ensemble of signal morphological classifiers 13 (artifact detectors). By continuously monitoring the impedance of the FP1 electrode 10 the Beta5 Observer's signal quality can be assessed. The FP1's signal quality is combined with Beta5 analysis 9 and evaluation 11 by the Beta5 Observer and propagated to the Observation Mediator. The outputs of the Signal Morphology Classifiers are four artifact free EEG data streams and a declaration of the types of artifacts detected. Two of the artifact classifiers propagate information to Observers. The Eyeblink Observer 19 is notified of the number and types of eyeblinks detected in the four EEG channels. The Suppression Observer 20 is notified whether EEG suppression has been detected over the last time period. The artifact free EEG data is further processed by the PSI Discriminant Observer 18, which performs a more complex multiple component analysis that serves as the foundation of the consciousness algorithm. The four observations: Beta5, PSI Discriminant, Eyeblink and Suppression) are propagated to the Observation Mediator 25. The Mediator combines these observations with measures of signal quality and appropriateness of observations based on patient state into an update of the Patient State Index and the associated trend. The time course of the PSI is monitored and logic is applied to assess the patient's state and this information is fed back to the Observation Mediator. It is through the use of this Multiple Observer Model that a clinically functional measure of state of consciousness is realized.

The output of the Algorithm is a set of four processed parameters calculated every 2.5 seconds (each 2.5 second block is referred to as an epoch). These are the main output parameter, i.e., the Patient State Index (PSI); the Suppression Ratio (SR); the EMG index (EMG); and the Artifact Index (ART). The measures in addition to the PSI provide additional information to the instrument operator on either specific aspects of the patient state or data quality. These measures are shown in FIG. 2 to be directed to the User Interface. The Artifact Index is a measure of signal quality. The SR-Ratio is the percentage of time in the last minute the patient's EEG has been suppressed. The Beta2 component measure is related to the degree of muscle activity (EMG) detected. The outputs of this multiple observer based PSA 4000 algorithm is a periodic update of: the Patient State Index (the primary derived parameter), the Artifact Index, the Suppression Ratio and a measure of EMG activity.

The Patient State Index 164, the primary indicator of patient level of awareness, is 10 developed to characterize the relative state of consciousness of an anesthetized patient. The Algorithm outputs a periodic update of this primary parameter. The Algorithm provides for upper and lower thresholds of this parameter within which the patient will be said to be in an appropriate level of unconsciousness for surgery. (Other levels may be appropriate for other conditions such as intensive care sedation.) The PSI range is defined to be from 0 to 100, with higher values indicating a higher level of consciousness or awareness.

The Suppression Ratio 162 is an indicator of the relative amount of time that the patient's EEG waveforms exhibit a characteristic Burst Suppression pattern. The Burst Suppression pattern is accepted to be an indicator of deep levels of unconsciousness under sedation. In certain situations of traumatic head injury, for example, it is necessary to reduce the brain's need for oxygen by putting the patient into a drug induced (barbiturate) coma. This brain state is observed in the EEG as Burst Suppression. For most surgical procedures, burst suppression is considered an inappropriately deep level of sedation where the anesthesiologist would normally reduce drug flow rates accordingly. The Suppression Ratio is the percentage of epochs (2.5-second epochs) in the last one minute that have been declared as Suppressed Epochs.

The EMG Index 163 is an indicator of muscle activity. Under certain conditions, an EMG response may be interpreted as an indicator of the patient's response to pain or stress. The anesthesiologist's action would depend upon the conditions present when the EMG response occurs, as EMG is a normal indication at the end of surgery. During surgery, the anesthesiologist titrates additional hypnotic for stress or analgesic for pain accordingly. The EMG Index is a weighted percentage of half-epochs (over the past one minute) in which muscle activity, as measured by the power in the BETA-2 band, exceeds a threshold level. Newer epochs are weighted more heavily than the older ones.

The Artifact Index 165 is an indicator of data quality, or of the amount of artifacts present in the data. It is also a weighted percentage (over the past one minute). Increase in the artifact index is normal during any patient movement and may be associated with the use of certain equipment such as BOVI or train-of-four when applied to the face. Poor contact impedance aggravates all sources of artifact and will require intervention by the anesthesiologist to correct poor electrode contact with the patient.

BRIEF DESCRIPTION OF THE DRAWINGS

FIG. 3 shows the basic structure of the system.

DETAILED DESCRIPTION OF THE PREFERRED EMBODIMENT

THE HEADSET AND THE PATIENT MODULE

Figure 1:
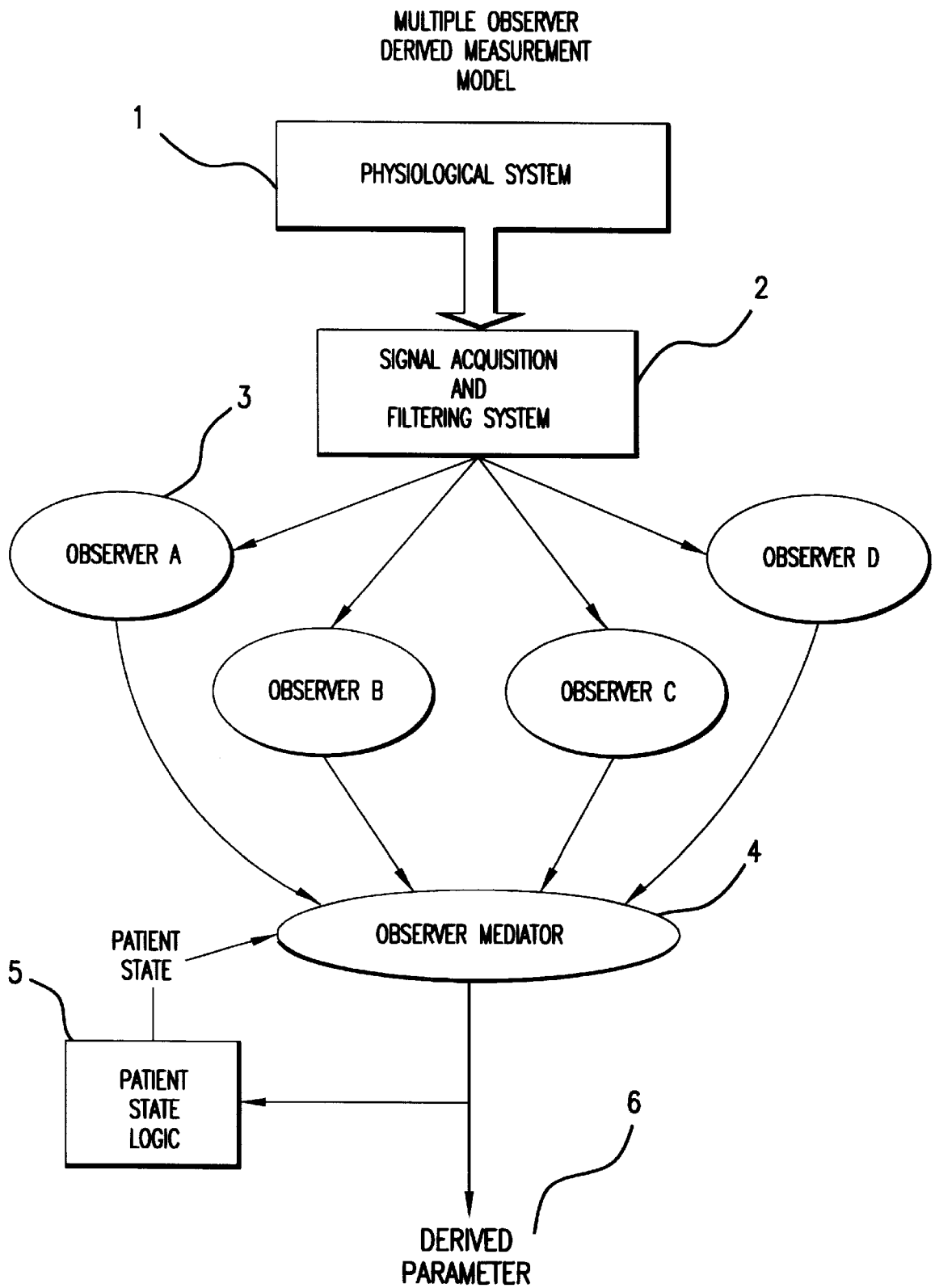
FIG. 1 portrays the basic structure of the Multiple Observer Model.
Figure 2:
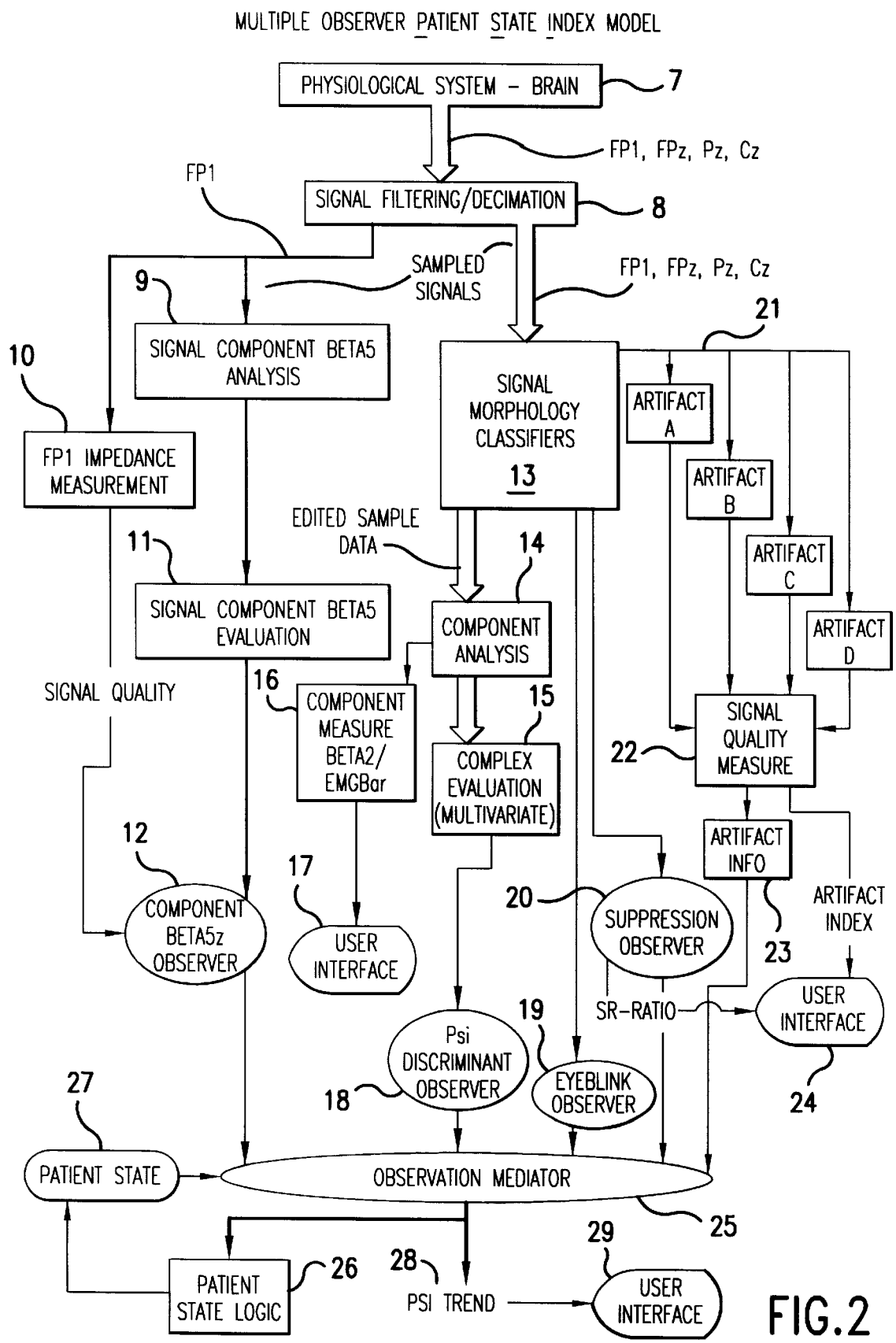
FIG. 2 is a more detailed illustration of the Multiple Observer Model.
Figure 4B:
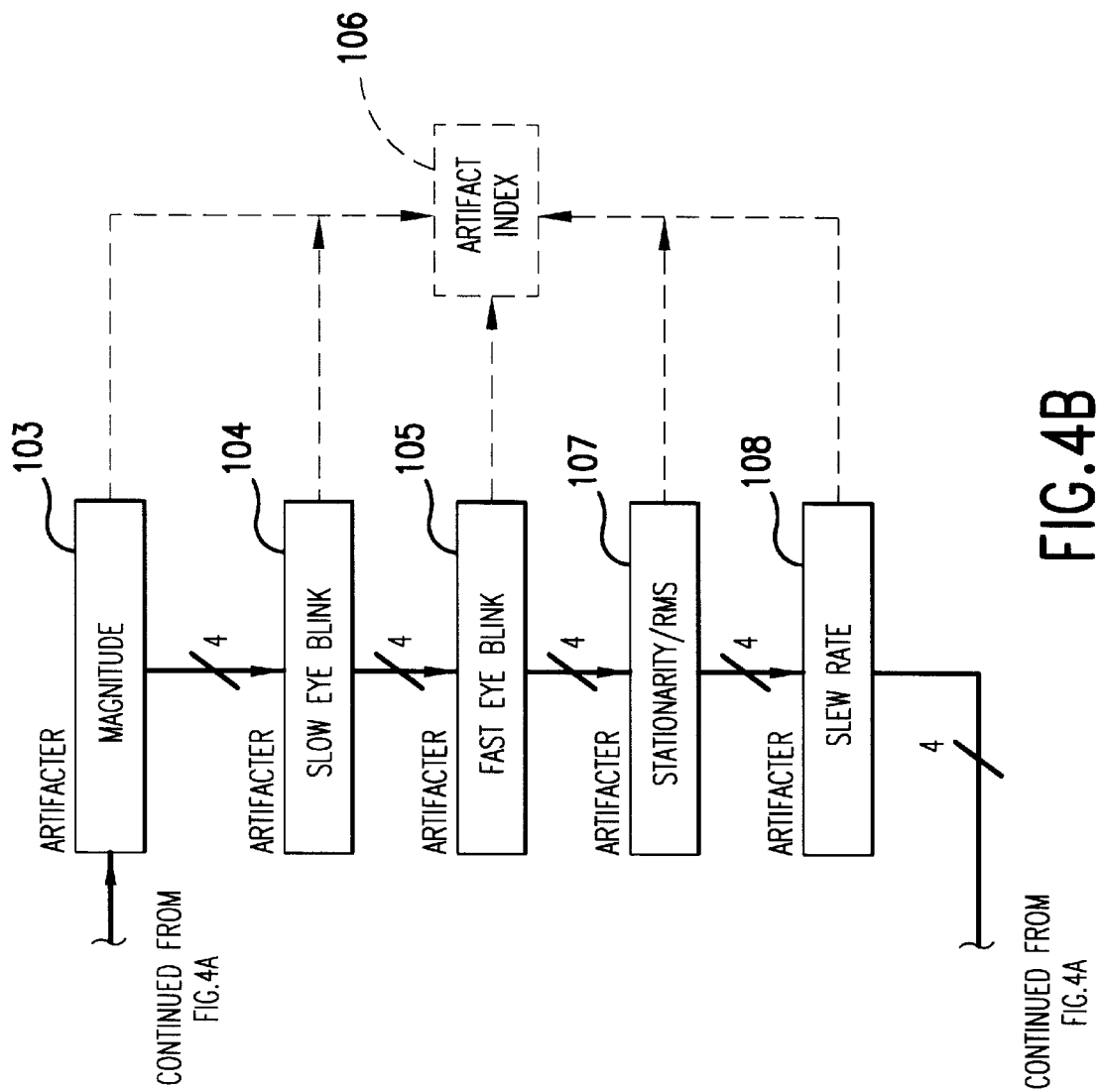
FIG. 4 shows the basic logical flow of the Algorithm.

In a related previous application, Ser. No. 09/113,946, filed Jul. 10, 1998, incorporated herein by reference as though fully set forth, one of the current inventors and others described a head set which can extract from the patient's head EEG signals from five favored locations of the set of international standard locations. The five favored locations are denoted in the international system by Fp 1, Fp2, Fpz', Cz, and Pz. In current embodiments these are electrically referenced to linked ear or linked mastoid contacts. EEG data from four of these five specific locations are analyzed. Alternatively, a more elaborate headset, such as that disclosed by Imran, U.S. Pat. No. 5,479,934, issued Jan. 2, 1996, can be used to obtain information from the four desired locations.

As shown in FIG. 3, the PSA Patient Interface consists of a Patient Module 42, patient interface cable 43, and a Patient Electrode Set 44 designed to provide a superior quality, programmable patient interface for EEG monitoring in the OR and ICU. The Patient Module is housed in a custom molded plastic enclosure with an integral universal-mounting bracket that facilitates attachment to an IV pole, bed sheet or rail. A detachable patient interface cable provides a quick connect/disconnect capability to the PSA appliance or Patient Module. EEG signals from the appliance are acquired with an isolated instrumentation grade, 4-channel pre-amplifier assembly and programmable multiplexed high speed A/D converter. The signal inputs are acquired referentially with reformatting provided by the Host application if necessary. Preamplifier optimization for EEG is standard, with EP and ECG optional by design. The combination of optically isolated data pathways, a low leakage/high isolation power converter and amplifiers with precise gain and band-pass matching results in greater than 120 dB CMRR. Calibration, Impedance Test, and Normal Operation are remotely controlled through the DSP Interface using commands generated by the Host Application. A full duplex connection is provided between the Patient Module and the DSP via dual optical-isolators that comply with VDE0884 for safety with extremely low leakage. The power converter is a UL Listed & Medical Grade. This extreme isolation results in negligible leakage currents and assures IEC601/UL2601 compliance with superior common mode performance.

The proprietary ISA bus DSP card provides a real time interactive link between the host and patient module and manages the acquisition, calibration and impedance functions of the patient module. Balanced differential drivers are used to minimize EMI associated with serial data transmission while providing the ability to extend the link to approximately 1000 feet. Filtering and decimation of the acquired data takes place in the DSP.

THE ANALYSIS UNIT

The PSA 4000 analysis unit embodies and operates by means of a complex Algorithm referred to hereafter as the PSA 4000 Algorithm. The system operates in three distinct modes, sometimes referred to as states, with different characteristics. The three states are labeled as follows: 1) Data Accumulation; 2) Awake Patient; and 3) Unconscious Patient. Two very specific and well-defined events cause the transition of the system among these four states. These events are labeled as: 1) Sufficient Data Accumulated; and 2) Loss of Consciousness. The identification of events and the switching among the states at the occurrence of an identified event is described further below following the description of the operation of the PSA 4000 Algorithm.

The following notation is used in describing EEG data:

| | |
|---|---|
| Sample | A sample is actually a set of four values, one for each of the electrode, associated with a particular instant of time. |
| j | All samples have a sample index, denoted by j that increases with time. |
| j = 0 | The index of the most recent sample has index 0. All other samples therefore have a negative index. |
| $t_j$ | The time associated with a particular sample set is denoted by $t_j$. The time resolution of the algorithm neglects the miniscule differences between time values of electrode values in a sample. |
| $S_j$, S(j) | The sample associated with a particular index j. |
| S($t_j$) | The sample associated with a particular time. |

The basic operational modules of the PSA 4000 Algorithm are: EEG Data Collection, Filtering and Decimation; Artifact Detection and Signal Morphology Analysis; Eye-blink Observation; Suppression Observation; Calculation of Artifact Index; Calculation of Suppression Ratio Index; FFT Calculation; Spectral Band Decomposition; Calculation of the EMG Index; EMG Beta-5 Observation; Discriminant Observer Calculation of the Probability of Correct Classification; Observer Mediation for the PSI; and Display of the PSI, the Suppression Ratio Index, the EMG Index, and the Artifact Index.

Operational Modules
1) EEG Data Collection, Filtering and Decimation

The patient module (PM) 42 acquires EEG data at a sampling rate of 2500 Hz. The sampling and processing are established to produce a frequency representation resolution of 0.25 Hz or better.

Figure 5:
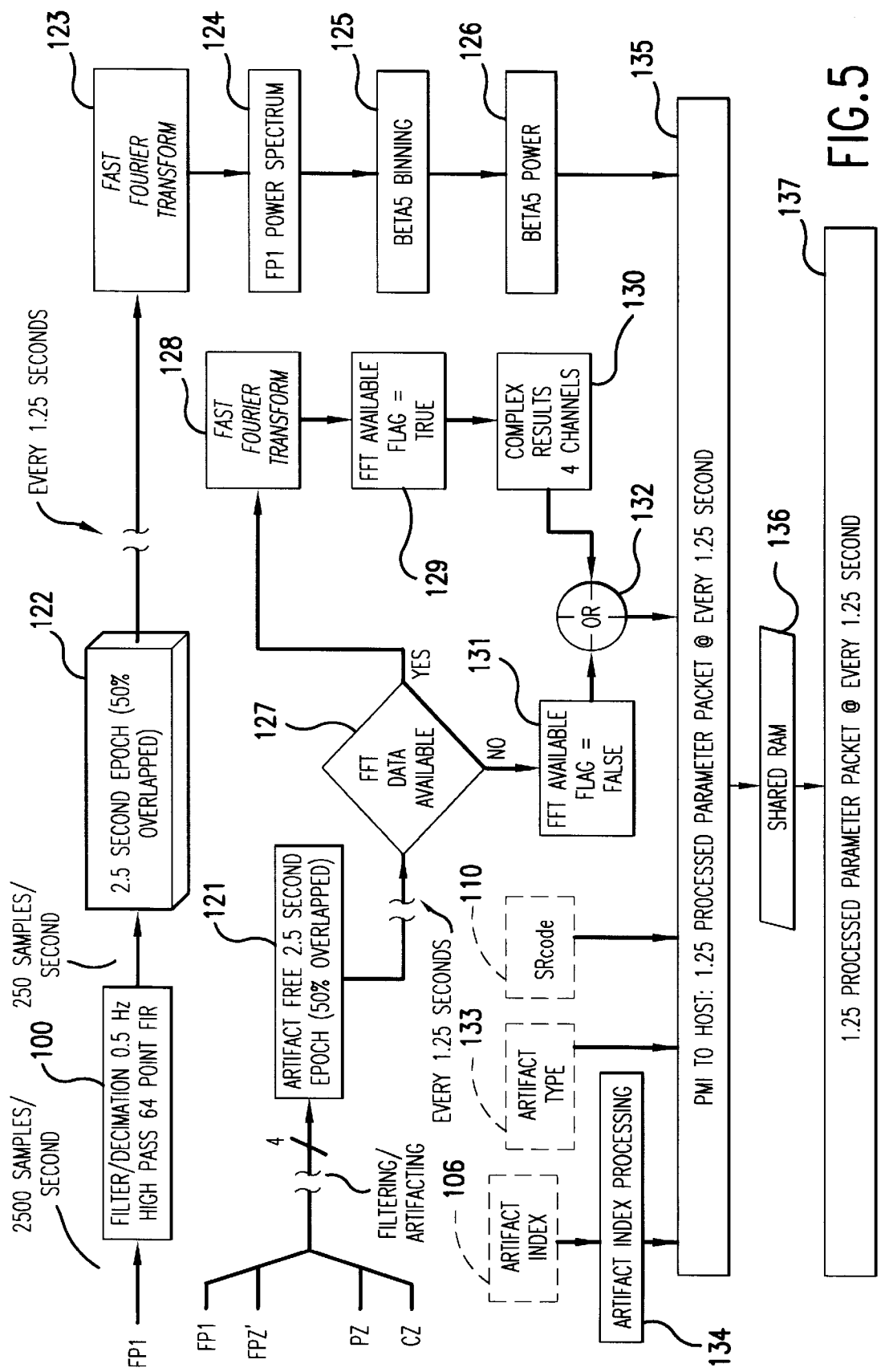
FIG. 5 continues and supplements the logical flow diagram of the Algorithm.
Figure 6A:
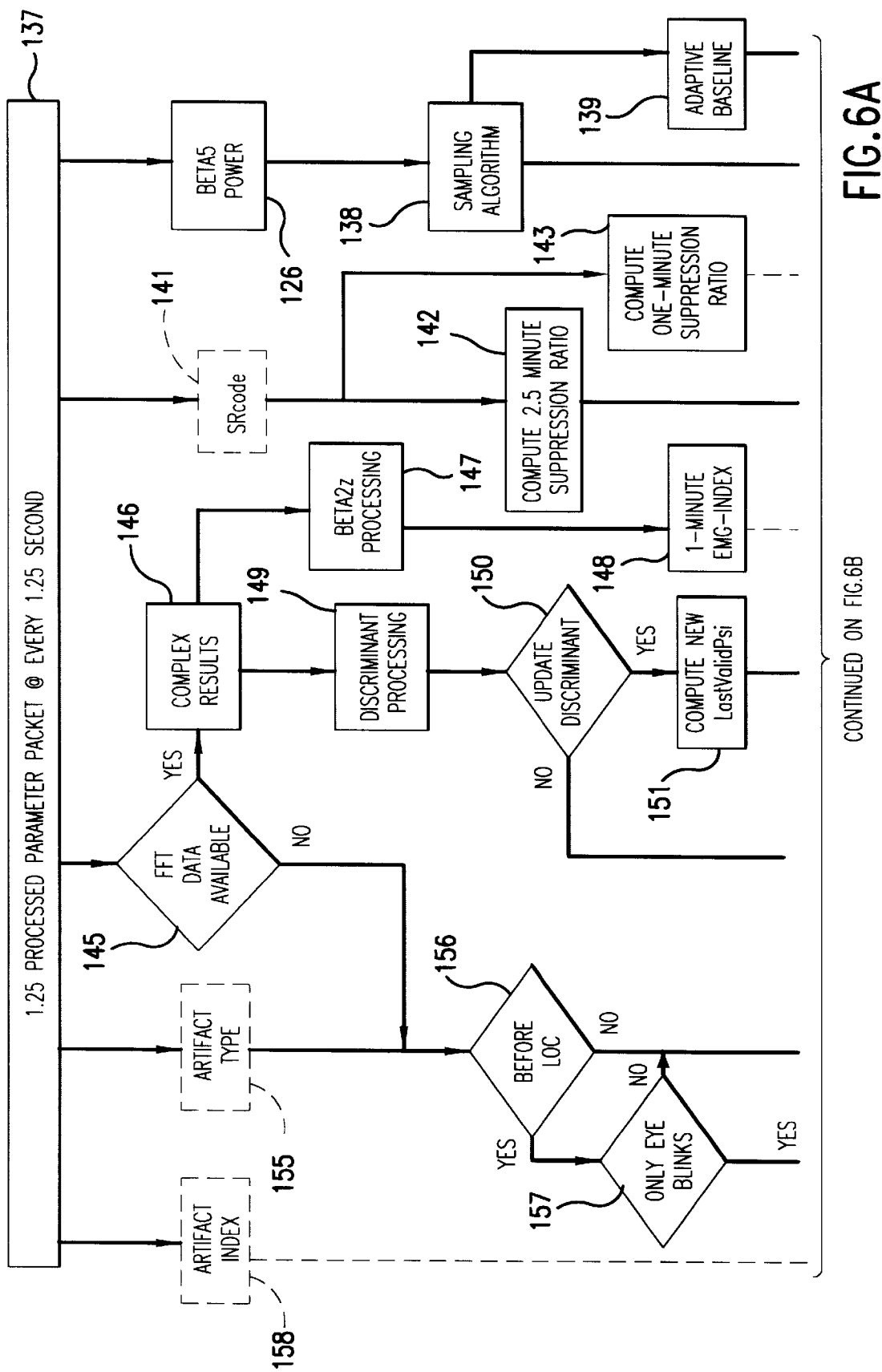
FIG. 6 shows the final stages of the logical flow of the Algorithm.
Figure 6B:
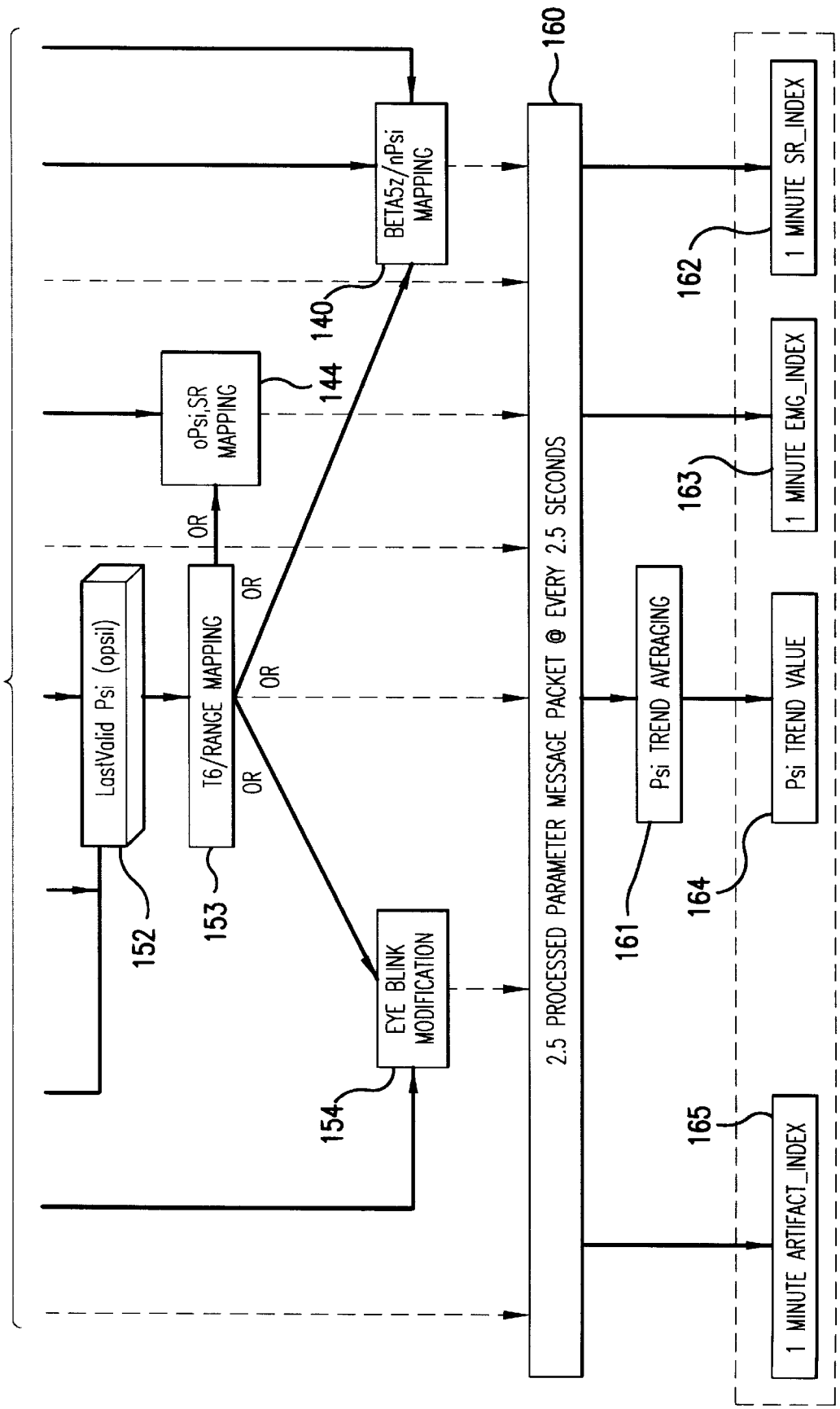

Data on four channels from the headpiece are filtered and decimated by a 10-to-1 low pass decimation filter 100, as shown in FIG. 5. This is done every 10 samples resulting in 1 sample every $\frac{1}{250}$ sec., for an effective sampling rate of $f_s$=250 Hz. After the 10-to-1 decimation and filter, the EEG data passes through a high-pass filter 102 with a cut-off frequency of $f_h$=0.4 Hz. The most recent $L_1$ samples are used, where $L_1$=$f_s/f_h$=625. Filtering starts at the sample s(−½L1) i.e., samples more recent than s(−½L1) are not filtered. The average of the most recent L1'−625 samples is subtracted from sample s(−½L1). We denote the filtered sample by s(−½L1):

$$s'\left(-\frac{1}{2}L_1\right) = s\left(-\frac{1}{2}L_1\right) - \frac{1}{L_1}\sum_{j=-L_1+1}^{0} s'(j) \qquad 1$$

Figure 7:
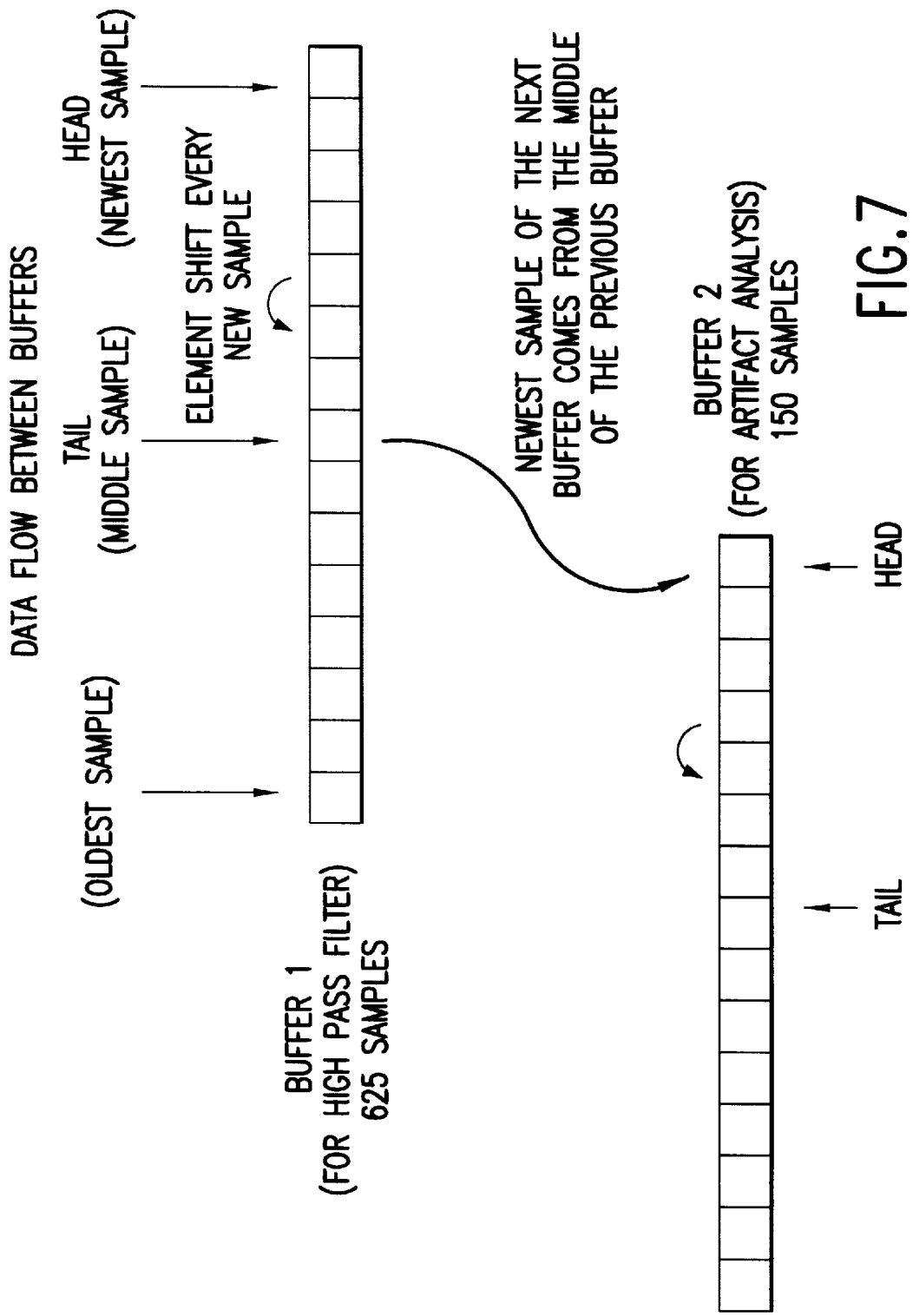
FIG. 7 depicts the flow of information between buffers.

The filtered sample is stored in the buffer as shown in FIGS. 7 and 8 and refreshed every half epoch.
2) Artifact Detection and Signal Morphology Analysis Artifact detection and analysis are performed once every sample, i.e., 250 times per second in an Artifacter Bank 103–108. This analysis results in an artifact type being associated with every sample that is classified as being affected by an artifact. Artifact types are also collated on an epoch-by-epoch basis. Artifact analysis is performed only on filtered samples. As shown in FIG. 5, after the high-pass filter, the artifact engine analyzes data on four channels for 5 kinds of artifacts:

a. Magnitude 103
b. Slow Eye Blink 104
c. Fast Eye Blink 105
d. Slew rate 107
e. Stationarity 108.

These are later combined in an Artifact Index module 106.

As is illustrated in FIG. 7, artifact analysis is done on a series of sample sets (sample buffers) of varying sizes. The magnitude, suppression, slew rate, and eye blink artifacts are checked on a buffer of 150 samples. These 150 samples (0.6 seconds) are older than the latest 312 of the 625 samples that have gone through the high-pass filter. Thus, they are identical with the newest 150 samples in the older half of the high-pass filter buffer. Similarly, the nms deviation artifact is checked on the 2000 samples (8.0 seconds) before (older than) the latest 75 of the 150 samples that were checked for the previous artifact types.

The conditions used in checking for the various types of artifacts are:
i) Magnitude The magnitude of the newest filtered sample is checked, on each of the four channels 103. (Recall that the latest filter sample is older than the latest sample by L½ samples.) If the magnitude of at least one of the channels exceeds a set threshold, the sample is classified as a magnitude artifact. Thus the condition is $$|s'(-½L_1)| > M_{thresh} \qquad 2$$

where $M_{thresh}$ is the magnitude threshold. The magnitude threshold is different for different channels and is determined empirically.
ii) Slew Rate The slew rate detector 107 checks for sudden changes in the magnitude of samples. The rate of change cannot be greater than 15 μV over 20 ms. To check this, the detector obtains the largest sample and the smallest sample over the $\delta_{slew}$ samples older than $s'(-\frac{1}{2}L_1-\frac{1}{2}L_2)$. If the difference between sample $s'(-\frac{1}{2}L_1-\frac{1}{2}L_2)$ and either the largest or the smallest sample is greater than 15 µV, than a slew rate artifact is declared. Mathematically, the conditions can be expressed as:

$$s'(-\tfrac{1}{2}L_1-\tfrac{1}{2}L_2)-\min(-\tfrac{1}{2}L_1-\tfrac{1}{2}L_2-\delta_{slew},-\tfrac{1}{2}L_1-\tfrac{1}{2}L_2) > L_{thresh} \quad 3$$

$$\max(-\tfrac{1}{2}L_1-\tfrac{1}{2}L_2-\delta_{slew},-\tfrac{1}{2}L_1-\tfrac{1}{2}L_2)-s'(-\tfrac{1}{2}L_1-\tfrac{1}{2}L_2) > L_{thresh} \quad 4$$

where $L_{thresh}$ is threshold for the slew rate artifact, equal to 15 µV. If either one of these conditions is satisfied, a slew rate artifact is declared. iii) Stationarity The stationarity artifact is checked 108 on the $L_3=2000$ samples (8.0 seconds) before (older than) sample $s'(-\frac{1}{2}L_1-\frac{1}{2}L_2)$. First the sum of the squares of the samples (not the squares of the deviations) is calculated. This is compared to the sample in the middle of the 2000 samples $s'(-\frac{1}{2}L_1-\frac{1}{2}L_2-\frac{1}{2}L_3)$. The following condition is checked:

$$s'\left(-\tfrac{1}{2}L_1-\tfrac{1}{2}L_2-\tfrac{1}{2}L_3\right) > \mathrm{bigger}\left(f_{scale}\sum_j [s'(j)]^2, f_{limit}\right) \quad 5$$

If this condition is satisfied for a given scale factor and limit term then a stationarity artifact is declared.
3) Eyeblink Observation The conditions for eye blinks, 104 and 105, are checked only if the slew rate artifact is not detected because the slope required in a slew rate artifact is larger than the slope required for eye blinks The eye blink observer is mathematically similar to the slew rate detector, however, it checks for both positive and negative slopes together, i.e., it checks for EEG humps within certain parameters.

First, the observer checks for the conditions on the rise (the first half of the eyeblinks). For small eye blinks, the artifactor checks the $\delta_{EBSb}$ samples older than sample $s'(-\frac{1}{2}L_1-\frac{1}{2}L_2)$ and obtains the largest and smallest samples. The following conditions are checked:

$$s'(-\tfrac{1}{2}L_1-\tfrac{1}{2}L_2)-\min(-\tfrac{1}{2}L_1-\tfrac{1}{2}L_2-\delta_{EBSb},-\tfrac{1}{2}L_1-\tfrac{1}{2}L_2) > L_{thresh} \quad 6$$

or $$\max(-\tfrac{1}{2}L_1-\tfrac{1}{2}L_2-\delta_{EBSb},-\tfrac{1}{2}L_1-\tfrac{1}{2}L_2)-s'(-\tfrac{1}{2}L_1-\tfrac{1}{2}L_2) > L_{thresh} \quad 7$$

If at least one of these conditions is satisfied, then the conditions on the second half of the eye blink are checked. The observer checks the $\delta_{EBSa}$ filtered samples newer than sample $s'(-\frac{1}{2}L_1-\frac{1}{2}L_2)$ and obtains the largest and smallest samples. One of the following conditions must be satisfied:

$$s'(-\tfrac{1}{2}L_1-\tfrac{1}{2}L_2)-\min(-\tfrac{1}{2}L_1-\tfrac{1}{2}L_2,-\tfrac{1}{2}L_1-\tfrac{1}{2}L_2+\delta_{EBSa}) > L_{thresh} \quad 8$$

or $$\max(-\tfrac{1}{2}L_1-\tfrac{1}{2}L_2-\delta_{EBSb},-\tfrac{1}{2}L_1-\tfrac{1}{2}L_2)-s'(-\tfrac{1}{2}L_1-\tfrac{1}{2}L_2) > L_{thresh} \quad 9$$

If (Equation 6 or Equation 7) AND (Equation 8 or Equation 9) is satisfied, then a small eye blink is declared. Similarly, for large eye blinks, the conditions are:

$$s'(-\tfrac{1}{2}L_1-\tfrac{1}{2}L_2)-\min(-\tfrac{1}{2}L_1-\tfrac{1}{2}L_2-\delta_{EBSb},-\tfrac{1}{2}L_1-\tfrac{1}{2}L_2) > L_{thresh} \quad 10$$

or $$\max(-\tfrac{1}{2}L_1-\tfrac{1}{2}L_2-\delta_{EBLb},-\tfrac{1}{2}L_1-\tfrac{1}{2}L_2)-s'(-\tfrac{1}{2}L_1-\tfrac{1}{2}L_2) > L_{thresh} \quad 11$$

AND $$s'(-\tfrac{1}{2}L_1-\tfrac{1}{2}L_2)-\min(-\tfrac{1}{2}L_1-\tfrac{1}{2}L_2,-\tfrac{1}{2}L_1-\tfrac{1}{2}L_2+\delta_{EBLa}) > L_{thresh} \quad 12$$

or $$\max(-\tfrac{1}{2}L_1-\tfrac{1}{2}L_2,-\tfrac{1}{2}L_1-\tfrac{1}{2}L_2+\delta_{EBLa})-s'(-\tfrac{1}{2}L_1-\tfrac{1}{2}L_2) > L_{thresh} \quad 13$$

If (Equation 12 or Equation 13) AND (Equation 10 or Equation 11) is satisfied, then a large eyeblink is declared. The threshold parameters for eye blinks are determined empirically.
4) Suppression Observation Every time a new filtered sample is obtained, the suppression detector 109 looks at the sum of the squared deviations of samples over the latest filtered 600 milliseconds (150 samples, denoted by $L_2$) and over the latest filtered 20 milliseconds (5 samples, denoted by $L_5$).

For reference, the sum of the squared deviations, generically defined, is:

$$\Delta(j_1, j_2) = \left(\sum_{j=j_1}^{j_2} [s'(j)]^2\right) - \frac{1}{N(j_1, j_2)}\left[\sum_{j=j_1}^{j_2} s'(j)\right]^2 \quad 14$$

where $j_1$ and $j_2$ are sample indices, and $N(j_1)$ is the number of samples between these indices. This quantity is related to variance of the same sample set (the average of the sum of the squared deviations) through $$\sigma^2_{j_1,j_2} = \frac{\Delta(j_1, j_2)}{N(j_1, j_2)} \quad 15$$

The difference between these two sums of squared deviations is intended as an approximate measure of the power in the band between 1.67 Hz and 50 Hz. If, on any one of the four channels, this power is less than a set threshold, then a suppression-type artifact is associated with that sample. Thus the suppression condition is $$\Delta(-\tfrac{1}{2}L_1-L_2,-\tfrac{1}{2}L_1) - \Delta(-\tfrac{1}{2}L_1-L_5,-\tfrac{1}{2}L_1) < S_{thresh} \quad 16$$

where $S_{thresh}$ is the threshold for the Suppression Artifact. The thresholds are different for the different channels and are determined empirically.

(a) Persistent Suppression Ratio (SR)

The suppression Observer calculates a quantity called the persistent Suppression Ratio (pSR). It is defined as the percentage, over the past 2.5 minutes, of 2.5-second epochs in which a suppression artifact was detected. The pSR is used later in calculating the PSI from the PCC.

The pSR is also calculated based on 2.5-sec suppressed epoch declarations, even though 1.25-sec suppressed epoch declarations are available from the current overlapping-FFT scheme. (Recall that the connecting rule is, if one of the two 1.25-sec epochs in a 2.5-sec epoch is declared suppressed, then the 2.5-sec epoch is declared suppressed.) The pSR is used later in calculating the PSI from the PCC.
5) Calculation of Artifact Index The 2.5-second Artifact Index 106 is one of the four final output parameters communicated to the user of the PSA 4000. The Artifact Index is a time-weighted percentage of 48 overlapped epochs (1.25-second epochs) in the past one minute that were declared as artifacted epochs. The newer half-epochs are weighted more heavily than the older half-epochs. The Artifact Index is calculated every 1.25 seconds.
6) Calculation of Suppression Ratio Index The Suppression Ratio (SR) 143 is also one of the four final output parameters communicated to the user of the PSA 4000. The SR is defined as the percentage, over the past one minute, of 2.5-second epochs in which a suppression artifact was detected.

7) FFT Calculation

Whenever 625 continuous good (non-artifacted) samples are calculated, the FFT of the time series (i.e., the set of 625 samples, also called an epoch) is calculated. A Hamming Window is applied to the time series data before the calculation of every FFT (see references). EEG data is sliced into 2.5-second periods, called epochs, containing 625 samples each. The Fourier Transform of an epoch of EEG data is calculated. FFT calculations 126, 128 are done using a 50% overlap scheme, i.e., FFT calculations are done every 1.25-seconds for data covering the last good 2.5-second period.

8) Spectral Band Decomposition

The following band definitions are used in succeeding Algorithmic calculations 146. The band definitions are given in units of Hertz (Hz).

TABLE 1

| Band Name | Band definition (Hz) |
| --- | --- |
| $\Delta$ | 1.5–3.5 |
| $\theta$ | 3.5–7.5 |
| $\alpha$ | 7.5–12.5 |
| $\beta$ | 12.5–25.0 |
| $\beta_2$ | 25.0–50.0 |
| $\beta_5$ | 35.0–50.0 |
| Tot | 1.5–25.0 |

9) Calculation of the EMG Index

The EMG Index 148 is an indicator is a time-weighted percentage of 1.25-second epochs in the past one minute that had an $F_1\beta_2$ z-component of greater than 1.96. The newer half-epochs are weighted more heavily than the older half-epochs.

10) EMG BETA-5 observation

The $F_1\beta_5$ raw measure 126, is the power on the $F_1$ channel in the $\beta_5$ band. The $F_1\beta_5$ Z-component is the logarithm of the raw measure, and the $F_1\beta_5$ Z score is the population-normed Z-component. The $F_1\beta_5$ index is defined as a running average of the $F_1\beta_5$ Z-scores over the past twelve overlapped-epochs, in which the newest Z-score is limited to a maximum change of six population standard deviations from the latest running average.

11) Discriminant observer calculations

A discriminant 149 is a function of statistical variable that maximizes the separation, in the variable space, of two groups of interest. It is usually a linear combination of the statistical variables. Thus, definition of the discriminant involves both specification of the variables and their weights.

i) Raw Measures for the Discriminant Observers

The Raw Measures used by the discriminant observer 18 are defined by the following table:

TABLE 1

Raw Measures as a combination of electrodes and bands

| | tot | $\Delta$ | $\theta$ | $\alpha$ | $\beta$ | $\beta 2$ |
| --- | --- | --- | --- | --- | --- | --- |
| $FP_1$ | P | | | | | P |
| $FP_{z'}$ | F | | | P | P | |
| $C_z$ | | | | | P | P |
| $P_z$ | P | P | | P | | |

In this matrix, P refers to monopolar power and F refers to mean frequency. The raw measured are averaged over 32 overlapped-epochs.

ii) Components for the Discriminant Observer

The specific set of raw components calculated in the PSA 4000 Algorithm are as follows:

TABLE 2

Raw-components used in calculating the probability of correct classification

| Raw-Component # | QUANTITY | CHANNEL/BAND(S) |
| --- | --- | --- |
| 1 | monop abs power | $FP_1$Tot |
| 2 | mean frequency | $FP_{z'}$Tot |
| 3 | monop abs power | $P_z\alpha$ |
| 4 | power assymetry | $FP_1\ C_z\ \beta_2$ |
| 5 | monop power | $FP_{z'}\alpha$ |
| 6 | relative power | $P_z\Delta$ |
| 7 | monop power | $FP_{z'}\beta$ |
| 8 | monop power | $C_z\beta$ |
| 9 | monop abs power | $FP_1\beta_2$ |

The first 8 are used in calculating the PCC. The $9^{th}$ is used in calculating the final EMG Index output parameter. Z-components are obtained from the raw components by norming to a set of population means and standard deviations, which are obtained for each component from an experimental study of normative populations.

iv) Z-Scores

Z scores are either linear combinations of Z components, or identical to the z components. The z-score set used in the PSA 4000 discriminant is:

TABLE 3

Z-score set used in calculating the probability of correct classification

| Zscore # | Definition in terms of Z-components |
| --- | --- |
| 1 | monop power ($FP_1$Tot) |
| 2 | mean frequency ($FP_{z'}$Tot) |
| 3 | monop power ($FP_{z'}\alpha$) - monop power ($P_z\alpha$) |
| 4 | power assymetry ($FP_1\ C_z\beta_2$) |
| 5 | relative power ($P_z\Delta$) |
| 6 | monop power ($FP_{z'}\beta$) - monop power ($C_z\beta$) |

The z-scores are linearly combined with weights such that the linear combination will maximize the separation between the two statistical groups: a group of aware people and a group of anesthetized unaware people.

v) Calculation of the Probability of Correct Classification

The probability that a set of z-scores can be correctly classified as belonging to ar, aware group, as opposed to an anesthetized unaware group, is obtained from the discriminant by using a sleep term, $$S = c_s + \sum_{i=1}^{6} w_i^{(S)} z_i \qquad 17$$

where $c_s$ is a constant term and the w's are discriminant weights. Similarly, the wake term is $$W = c_w + \sum_{i=1}^{6} w_i^{(W)} z_i \qquad 18$$

The probability of correct classification is $$PCC = \frac{e^W}{e^E + e^S} \qquad 19$$

The PCC, calculated every 1.25 seconds, is a rigorously defined mathematical probability, and as such, varies between zero and one.

12) Observer Mediation

Observation mediation logic 25 mediates between the different observers and indices to produce a final set of output parameters, including the PSI.

a) The Initial PSI

The initial PSI is the starting point for observer mediation logic and is simply a linear range expansion of the PCC by a factor of 100.

b) Variability Transformation of the Initial PSI

The initial PSI 152, also referred to as the oPSI, undergoes a piecewise-linear transformation 153 that re-scales it according to the following formula:

$$rPSI=1.7(oPSI)-70.0 \quad oPSI \geq 85.0$$

$$rPSI=0.7(oPSI)+15.0 \quad 85.0 > oPSI > 15.0$$

$$rPSI=1.7(oPSI) \quad 15.0 > oPSI \qquad 20$$

The result is termed the rPSI.

c) Mediation of Eye Blink Information

Eye blink information is incorporated into the PSI 154 only prior to LOC, and only if the rPSI is greater than the LOC threshold of 50. An epoch is considered an eye blink epoch only if there are also no other types of artifact detected.

If an eye blink epoch is detected during an Indeterminate Probability (i.e., before an rPSI can be calculated, because the raw measure buffer is not yet full) then an rPSI of 95 is reported. This rPSI and all succeeding rPSI values (until the buffer is full enough to calculate a value) are then treated as if they originated from a calculated probability, i.e., it undergoes the transformations and calculations that lead to the PSI. After this first eye blink, whenever an eye blink is detected, the current rPSI is averaged with 99, and the result becomes the current rPSI.

d) Mediation of Suppression Information

The new PSI that includes the information represented by the pSR is referred to as the nPSI. The nPSI is constructed as a function of the rPSI and the pSR, denoted as nPSI(pSR, rPSI) 144.

The transformation when pSR=0, i.e., nPSI(0, rPSI), is an important special case of the whole transformation. Its result is a compression of the rPSI range (0–100) into a new scale. The new, compressed scale has a minimum value, $nPSI_{bot}$, so that range of the new scale is ($nPSI_{bot}$–100). The re-scaling is chosen so that a rPSI of 15 maps to a nPSI of 25. This completely determines the transformation equation, because the maxima of the two scales are the same. The transformation is given by $$nPSI(0, rPSI) = \frac{15}{17} rPSI + nPSI_{bot} \qquad 21$$

where $nPSI_{bot}$ is given by $$nPSI_{bot} = 25 - \frac{15^2}{17} \cong 11.7647 \qquad 22$$

Another condition is the special case at pSR 15, i.e., nPSI(15, rPSI). We impose the condition $$nPSI(pSR=15, rPSI \geq 15)=15 \qquad 23$$

A third condition determining the transformation is case when pSR≧50. Then we have $$nPSI(pSR \geq 50, rPSI)=0 \qquad 24$$

e) Mediation of Beta5 Information

Incorporation of EMG information into the PSI is based on the $F_1\beta_5$ index 140. This modification is a refinement of the EMG information already in the PSI by virtue of the $F_1\beta_2$ term. EMG modifications are possible only when the pSR=0, and only after a time threshold of 15 minutes after the declaration of Loss Of Consciousness (LOC). EMG modifications are not possible when the patient module is disconnected. In addition, there is a timeout period of ⅓ minute after the end of the PM Disconnect during which EMG modifications are not possible. When a BAD IMPEDANCE is detected, the EMG power used is the last one calculated before the BAD IMPEDANCE condition.

The PSI that incorporates possible changes due to the $F_1\beta_5$ index is called the tPSI. (The tPSI is a function of EMG and the nPSI.)

When the PSI is modified by the $F_1\beta_5$ index then the tPSI is considered a good data point and is painted non-white, even though the underlying PSI may have been artifacted and would have otherwise been painted white. The PSI is considered modified by EMG only when the change is greater than 1.

The change from nPSI to tPSI is calculated using the following equation: we express the change as the product of three functions:

$$\Delta PSI = f(F1\beta5) g(nPSI) h(F1\beta5, nPSI) \qquad 25$$

The first function governs the rise along the $F_1\beta_5$ axis:

$$f(F1\beta5) = \left( \frac{1}{1 + e^{-(F1\beta5 - B_m)/B_w}} \right) \qquad 26$$

The second function governs the rise along the nPSI axis:

$$g(nPSI) = \left( \frac{1}{1 + e^{-(nPSI - P_m)/P_w}} \right) \qquad 27$$

The third function limits the change as nPSI becomes bigger, because there is a smaller remaining range of tPSI into which to change.

$$h(F1\beta5, nPSI) = t_c - \frac{t_c}{n_c + \frac{100 - n_c}{1 + e^{-(F1\beta5 - b_m)/b_w}}} nPSI \qquad 28$$

In each of the three functions there is a functional form $F(x) = (1 + \exp((x+c)/d))^{-}$.

This function creates a rising transition from 0 to 1, with the midpoint of the transition occurring at x=c, and the width (or sharpness) of the transition determined by d.

Thus the first of the three equations above defines the contribution of the $FP_1\beta_5$ index as rising from zero around an index of approximately 1.25, and the second factor defines that the change can only occur be significant at nPSI values starting around a value of 19.

The third factor in the equation embodies the idea that as the nPSI gets larger, there is a smaller and smaller remaining range into which the tPSI can change. The change is limited to only part of this remaining range. The maximum of this limiting part is defined by the last term which also has the functional form of f(x). The maximum is itself a rising function of the $FP_1\beta_5$ index with a midpoint at a large value of 10.25 and a relatively large transition width of 3.0. This means that for most typical values of the $FP_1\beta_5$ index, the change is limited to a maximum value of about 80. This maximum will increase as the $FP_1\beta_5$ index increases.

The tPSI is given by $$tPSI = nPSI + \Delta PSI \qquad (29)$$

The EMG B5 baseline is adaptively determined as follows: The EMG B5 index over the past three minutes is stored in two windows, or buffers. The first holds the indices for the oldest two minutes (of the three minutes) and the second holds the most recent 1 minute (of the three minutes). For each of these windows, the averages and standard deviations are calculated at every update (every 1.25 seconds).

Every update, the following conditions on the averages and standard deviations are checked:

$$(F_1\beta_5)_1 < A_1 \qquad (30)$$

$$|(F_1\beta_5)_1 - (F_1\beta_5)_2| < D \qquad (31)$$

$$\sigma_1 < S_1 \qquad (32)$$

$$\sigma_2 < S_2 \qquad (33)$$

If all four conditions are satisfied, then the adaptive baseline, L, is set to the average in the first window, $A_1$:

$$L = A_1 \qquad (34)$$

The variable A in the equation above has a value of A=1.25−baseline. The baseline in the beginning of the case is set to zero (the population baseline, since the EMG B5 z-scores used have been normalized to the population baseline). However the EMG B5 term is continuously monitored for conditions that will allow the setting of a new baseline. This allows the adaptation of EMG B5 modifications to individual patient differences. The adaptive baseline algorithm is described later in this section.

f) Mediation of Artifact Information i) Repeated PSI

The conditions for declaring a Repeated PSI are distinct from the conditions for Repeated Probabilities. A Repeated Probability is generated if artifacts make an FFT unavailable. However, several things can cause the PSI to vary even if the underlying probability is a repeated probability. First, eye blink information can modify the oPSI'. Secondly, the NPSI can be calculated from repeated probabilities. If the pSR happens to change during repeated probabilities, the nPSI will vary even if the underlying probability does not. Third, EMG modifications can also be active during repeated probabilities.

The following conditions are used in the declaration of a Repeated PSI: if an epoch is an artifacted epoch, AND the PSI has NOT been modified by either eye blinks or EMG, AND the Artifact Index is greater than 30, then the tPSI is a Repeated PSI. "Repeated PSI" is merely terminology, carried over from "Repeated Probability". It does not imply that the PSI is necessarily repeated.

ii) Artifacted PSI

Artifacted PSI's are distinct from Repeated PSI's. The Artifacted PSI declaration is made on the 2.5-second PSI values. Repeated 1.25-second PSI's or repeated full-epoch PSI's are possible (through the rules in the previous sections). A 2.5-second PSI is declared an Artifacted PSI if the 2.5 second PSI is a repeated PSI AND the Artifact Index is greater than 30.

iii) Trend PSI

The Trend PSI is the running average of four 2.5 second PSI's, whether it is an Artifacted PSI or not. In the beginning of the case, the initial value of the running average is the population value of 95 for awake patients. The Trend PSI is the one of the four output parameters of the PSI 4000 Algorithm.

SYSTEM STATES AND SWITCHING

As previously noted, the system operates in three distinct modes, each operating significantly differently. The three specifically defined states are as follows.

1) States a) Data Accumulation

During Data Accumulation, the raw measure buffer of raw measure sets does has less than 24 overlapped-epochs of raw measure sets stored. EEG data acquisition is being performed, artifact analysis is being done, and FFT calculations are being made on good data. Each calculated raw measure set is added to the raw measure buffer. The following are NOT calculated: raw components, Z components, the PCC, and the PSI, and the EMG Index. The SR and the Artifact Index are calculated during this period.

b) Awake State

In Awake State, the raw measure buffer has 24 or more (up to 32) overlapped-epochs of raw measure sets stored. EEG data acquisition is being performed, artifact analysis is being done, and FET calculations are being made on good data. If the raw measure buffer has 32 raw measure sets, the oldest raw measure set is thrown away before the most recently calculated measure set is added. During this mode, all four output parameters are calculated from non-artifacted data. The most notable feature of this mode is the incorporation of eye blink information from artifact analysis into the PSI.

c) Unconscious State

In Unconscious State, eye blink information is ignored and is NOT incorporated into the PSI. Otherwise, the operation of the Algorithm is the same as in Awake State.

2) Transition Events

The following three transition events initiate a transition between the four states.

a) Sufficient Data Accumulated

The Algorithm determines that sufficient data has been accumulated after the raw measure buffer has accumulated 24 overlapped-epochs of raw measure sets calculated from FFT data. FFT data can only be calculated from non-artifacted epochs. Thus the time spent in this state is variable, depending on the amount of artifacts present in the data.

b) Loss Of Consciousness

If the PSI has 18 consecutive non-repeated values below 50, Loss Of Consciousness is declared. This declaration is used to disable the incorporation of eye blink information into the PSI.

We claim:

1. An apparatus for classifying the level of awareness or anesthesia of a patient using electroencephalograph (EEG) signals, comprising:

a. a plurality of patient electrodes whereby a plurality of patient EEG signals is acquired;

b. a patient module connected to the patient electrode set; and c. an analysis unit connected to the patient module, said analysis unit comprising:

i. a plurality of modules comprising observers configured to produce measures of specific characteristics in the plural EEG signals; and ii. an observer mediator which mediates among plural outputs of the plural observers according to a mediation logic, whereby the observer mediator produces at least one output parameter characterizing the patient's state of awareness or anesthesia;

wherein one of the modules comprising an observer comprises a subsystem which constructs and sends to the observer mediator a statistical discriminant based on plural statistical variables derived from power and frequency information extracted from plural EEG signals.

2. The apparatus of claim 1 in which the plural modules comprising observers, other than the module comprising a subsystem which constructs a statistical discriminant, comprise plural classifiers which detect signatures within the plural EEG signals, which signatures are different from the statistical variables used to construct the statistical discriminant.

3. The apparatus of claim 2 in which the observer mediator weighs the output of the plural observers by monitoring each observer's input signal quality and the context of the observation based on the patient's state of awareness or anesthesia.

4. The apparatus of claim 1 in which one of the at least one output parameters is a Patient State Index which characterizes the patient's state of awareness or anesthesia.

5. The apparatus of claim 2 in which the plural classifiers comprise a corresponding plurality of artifact detectors.

6. The apparatus of claim 5 in which the plurality of artifact detectors comprises at least a magnitude artifact detector, a slow eye blink detector, a fast eye blink detector, a stationarity/RMS detector, and a slew rate detector.

7. The apparatus of claim 2 additionally comprising an additional separate channel transmitting a duplicate of one of the plural EEG signals to a Beta5 observer, the output of which is also directed to the observer mediator.

8. The apparatus of claim 6 additionally comprising a suppression classifier.

9. An apparatus for classifying the level of awareness of a patient using electroencephalograph (EEG) signals, comprising:
   a. a plurality of patient electrodes whereby a plurality of patient EEG signals is acquired;
   b. a patient module connected to the patient electrode set; and
   c. an analysis unit connected to the patient module,
      in which the patient module and the analysis unit each comprises a plurality of channels corresponding to the plurality of patient electrodes;
      in which each of the plurality of channels in the analysis unit comprises a plurality of modules comprising observers tuned to produce measures of specific characteristics in the plural EEG signals, the output of which observers is directed to a single observer mediator which combines the output of the plural observers in the plural channels into a single derived parameter; and
      in which the observer mediator weighs the output of the plural observers in the plural channels by monitoring each observer's input signal quality and the context of the observation based on the patient's state of awareness or anesthesia.

10. The apparatus of claim 9 in which the plural classifiers in each of the plural channels comprise a corresponding plurality of artifact detectors.

11. The apparatus of claim 10 in which the plurality of artifact detectors in each of the plural channels comprises at least a magnitude artifact detector, a slow eye blink detector, a fast eye blink detector, a stationarity/RMS detector, and a slew rate detector.

12. The apparatus of claim 9 additionally comprising an additional separate channel transmitting a duplicate of one of the plural EEG signals to a Beta5 observer the output of which is also directed to the observer mediator.

13. The apparatus of claim 11 additionally comprising a suppression classifier in each of the plural channels.

14. An apparatus for electronically estimating the level of a patient's awareness using electroencephalograph (EEG) signals comprising
   a. a predetermined number of plural channels for EEG data;
   b. a corresponding plurality of electrodes which acquire and transmit from the patient's head a plurality of EEG signals corresponding in number to the plural channels;
   c. an additional channel into which a duplicate signal of the signal in one of the predetermined plurality of channels is transmitted;
   d. in the additional channel, an overlapped epoch buffer;
   e. in the additional channel connected to the overlapped epoch buffer, a module producing the Beta 5 band power using a single channel fast fourier transform (FFT) generator and Beta 5 band binding;
   f. a decimator, and a high pass filter in each of the plural channels of EEG signals;
   g. a corresponding plurality of artifacter banks, one in each of the plurality of channels, each bank comprising a plurality of time domain artifact detectors;
   h. a Raw Time Series Data Buffer comprising a corresponding plurality of buffers storing a corresponding plurality of epochs of signals from the plural channels, each of the plurality of epochs of signals comprising overlapped partial epochs of partial epoch length signals from the corresponding plural channels;
   i. in each of the plural channels, an artifact type-categorizer;
   j. in each of the plural channels, a magnitude artifact detector as one of the plurality of time domain artifact detectors;
   k. in each of the plural channels, at least one eye-blink detector as at least one of the plurality of time domain artifact detectors;
   l. in each of the plural channels, a stationarity/RMS detector as one of the plurality of time domain artifact detectors;
   m. in each of the plural channels, a slew rate artifact detector as one of the plurality of time domain artifact detectors;
   n. in each of the plural channels, a suppression detector/classifier as one of the plurality of time domain artifact detectors;
   o. in each of the plural channels, an artifact index generator;
   p. in each of the plural channels, an FFT generator producing a corresponding plurality of channels of complex frequency domain parameters;
   q. an EMG Index generator comprising a Beta 2z band processor;
   r. an EMG Beta-5 Observer;
   s. an Artifact Index generator;
   t. a Suppression Ratio generator;
   u. a discriminant processor;
   v. an observer-mediation module producing a patient state index (PSI) from the outputs of other observers;
   w. a PSI trend averaging module;
   x. a display apparatus displaying the Artifact Index, the PSI Trend Value, the EMG Index, and the Suppression Ratio.

15. A method of classifying anesthetized patients according to their conscious state as determined from an analysis of volunteer data using the OAA/S scale by performing the steps of:
   a. analyzing artifacts in time domain EEG data resulting in the rejection of data contaminated by predetermined types of artifacts;
   b. generating artifact labels and parameters;
   c. generating the Fast Fourier Transform (FFT) of segments of EEG data resulting in a frequency domain representation of the EEG data and computing therefrom the signal power in predetermined frequency bands;
   d. applying statistical analysis to various measures in the predetermined frequency bands to provide a probability of classification into aware and unaware groups, with reference to population norns obtained from statistical studies of large normative populations;
   e. combining the results of statistical analysis with other observations of the patient state to provide a single quantitative index of the patient's conscious state.

16. A method for monitoring the state of anesthesia of a medical patient using electroencephalograph (EEG) signals, comprising:
   a. acquiring a plurality of EEG signals from a preselected corresponding plurality of channels electrically connected to a plurality of international standard locations on a patient's head;
   b. digitizing and decimating the EEG signals in each of the plurality of channels;
   c. applying a plurality of time domain artifact detection modules to the signals in the plurality of channels;
   d. applying an eye blink observer to the signals in each of the plurality of channels and determining from them epochs with eye blinks
   e. applying a burst suppression observer to the signals in each of the plurality of channels and determining therefrom a suppression code;
   f. storing overlapped half-epoch decimated EEG signals in a buffer;
   g. performing a fast fourier transform with a resolution of 0.25 Hz or better on half epochs and epochs having no artifact label;
   h. using the fast Fourier transform results to compute a predetermined plurality of power measures for predetermined frequency bands;
   i. developing a classification probability by statistical analysis of the power measures;
   j. applying an EMG Beta-5 observer to the power measures
   k. determining a suppression ratio, an EMG index, and an artifact index;
   l. applying mediation logic to the results of all observers and indices, resulting in the patient state index,
   m. displaying the patient state index, the suppression ratio, the EMG index, and the artifact index on a display unit;
   n. administering anesthesia to the patient;
   o. repeating steps a. through l. at predetermined intervals and displaying the patient state index, the suppression ratio, the EMG index, and the artifact index on a display unit in a time ordered sequence;
   p. adjusting the anesthesia administered to the patient so as to attain a plane of anesthesia selected by the anesthesiologist; and
   q. adjusting the anesthesia administered to the patient in response to changes in the patient state index, the suppression ratio, the EMG index, and the artifact index.

17. A method for monitoring the state of anesthesia of a medical patient using electroencephalograph (EEG) signals, comprising:
   a. decimating incoming EEG signals;
   b. performing artifact analysis on the time domain EEG signals for validity and contamination;
   c. setting artifact codes and calculating artifact-related quantities;
   d. applying an eye blink observer and a suppression observer;
   e. determining the Fast Fourier Transform coefficients of the EEG data for each of the four channels;
   f. dividing the FFT spectral data into a plurality of frequency bands, and determining raw measures (either power or mean frequency) for the frequency bands;
   g. applying an EMG Beta 5 observer to these raw measures;
   h. applying statistical discriminant analysis to these raw measures, and determining a probability of correct classification into an aware population group;
   i. combining the probability with the results of other observers of the patient state to produce the Patient State Index (PSI).

18. A method for monitoring the state of anesthesia of a medical patient independent of the anesthetic agent comprising the steps of
   a. analyzing information in the frequency range of 0.5 Hz to 50 Hz;
   b. removing noisy or invalid data so as to provide artifact free frequency domain representations of EEG signals;
   c. extracting from the artifact free frequency domain representations specific frequency domain raw signal measures;
   d. applying a set of observers to both the time-domain data and frequency-domain measures;
   e. monitoring and evaluating these measures over time and providing statistical analysis of particular components of a montage of EEG signals;
   f. deriving a set of four processed parameters every epoch: the Patient State Index characterizing the relative state of consciousness of an anesthetized patient; the Suppression Ratio indicating the relative amount of time that the patient's EEG waveforms exhibit a characteristic Burst/Suppression pattern; the EMG index (EMG) indicating muscle activity as a weighted percentage of half-epochs (over the past one minute) in which muscle activity, as measured by the power in the BETA-2 band, exceeds a predetermined threshold level; and the Artifact Index indicating data quality or the amount of artifacts present in the data;
   g. scaling the Patient State Index so that it has a range of 0 to 100; and
   h. providing upper and lower thresholds of the patient state index within which the patient will be said to be in an appropriate level of unconsciousness.

* * * * *